US00PP10558P

United States Patent [19]

Durand

[11] Patent Number: Plant 10,558

[45] Date of Patent: Aug. 18, 1998

[54] JAPANESE ELM TREE NAMED 'DISCOVERY'

[75] Inventor: J. Richard Durand, Portage la Prairie, Canada

[73] Assignee: Bailey Nurseries Inc., St. Paul, Minn.

[21] Appl. No.: 814,036

[22] Filed: Mar. 10, 1997

[51] Int. Cl.[6] ..... A01H 5/00

[52] U.S. Cl. ..... Plt./53.3

[58] Field of Search ..... Plt./53.3

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

A new cultivar of Japanese elm tree (ie., *Ulmus davidiana* Japonica) is provided that exhibits excellent form and resistance to Dutch elm disease. Unlike other Japanese elm trees the growth habit is clean, symmetrical, upright, and vase-shaped. The foliage is obovate to oval in configuration and is slightly smaller than is typical for the species. Good cold hardiness and resistance to elm leaf beetles are exhibited. The new cultivar is particularly suited for growing as an attractive landscape shade tree.

2 Drawing Sheets

SUMMARY OF THE INVENTION

The original Japanese elm tree of the new cultivar was selected during 1985 from among approximately 500 seedlings of *Ulmus davidiana* Japonica that were being grown for testing and evaluation at Treherne, Manitoba, Canada. The seeds used to create the test planting were harvested from open-pollinated trees of the same species growing at the Agriculture Canada, Morden Research Station, Morden, Manitoba, Canada. The trees from which the seeds were harvested are believed to have been derived during the late 1930s from a Northern Manchurian source. A single plant of the new cultivar was discovered and was observed to possess the outstanding horticultural characteristics as described hereafter. This plant initially was designated No. 8502.

Following asexual propagation the new cultivar of the present invention has been further tested and evaluated at Prairie Shade Nursery, Portage la Prairie, Manitoba, Canada; Jeffries Nurseries Ltd., Portage la Prairie, Manitoba, Canada; the University of Toronto, Toronto, Ontario, Canada; North Dakota State University, Fargo, N. Dak., U.S.A.; and at Bailey Nurseries Inc., St. Paul, Minn., U.S.A.

It has been found that the new plant of *Ulmus davidiana* Japonica of the present invention exhibits the following combination of characteristics:

(a) exhibits an attractive symmetrical upright vase-shaped growth habit,
(b) forms foliage that is obovate to oval in configuration and is slightly smaller than is typical for the species,
(c) exhibits good cold hardiness, and
(d) is highly resistant to Dutch elm disease.

The excellent tree form and resistance to Dutch elm disease of the new cultivar are particularly noteworthy. The clean appearance of the tree is maintained throughout the growing season. The vigor of the plant has been observed to be slightly less than that of the species and is believed to contribute to making the new cultivar slightly hardier than a typical tree of the species. The symmetrical upright vase-shaped growth habit generally is manifest throughout the tree beginning at the initial lateral branch and extending to the top of the crown (as illustrated). The seeds of the new cultivar generally are typical of the species. The new cultivar also has been found to exhibit resistance to elm leaf beetles. It is anticipated that specimens of the new cultivar will assume a height and spread of approximately 35 to 40 feet when fully mature. However, no plant of the new cultivar has reached such full state of maturity to date.

When the new cultivar is compared to the 'Freedom' cultivar (non-patented in the United States), it is found that the new cultivar exhibits a symmetrical upright vase-shaped growth habit while trees of the 'Freedom' cultivar form an open crown with codominant lateral branching, the new cultivar exhibits smaller less serrated leaves than those of the 'Freedom' cultivar, and the new cultivar exhibits yellow fall foliage coloration in the absence of a reddish-purple tinge that commonly is observed on the leaves of the 'Freedom' cultivar. The good Dutch elm disease resistance of the new cultivar is believed to be substantially identical to that of the 'Freedom' cultivar. The 'Freedom' cultivar is understood to have been earlier derived from same general germplasm pool as the new cultivar of the present invention.

The new cultivar of the present invention well meets the needs of the horticultural industry. It can be grown to advantage as an attractive landscape shade tree that can be maintained with relative ease.

The characteristics of the new cultivar have been shown to be homogeneous and stable under a number of different environments as indicated above. Beginning in 1988 at Portage la Prairie, Manitoba, Canada, the characteristics of the new variety have been shown to be fully transmissible by asexual propagation using whip and tongue grafting and by micropropagation via tissue culture.

The new plant of the present invention has been named the 'Discovery' cultivar.

BRIEF DESCRIPTION OF THE PHOTOGRAPHS

The accompanying photographs show, as nearly true as it is reasonably possible to make the same in color illustrations of this character, typical specimens of the plant and plant parts of the new cultivar. The Japanese elm specimens depicted in the photographs were being grown at Portage la Prairie, Manitoba, Canada.

DETAILED DESCRIPTION

The chart used in the identification of colors is that of The Royal Horticultural Society (R.H.S. Colour Chart). Common color terms are to be accorded their ordinary dictionary significance. The description is based on the observation of a test planting of the new variety while being grown at Portage la Prairie, Manitoba, Canada.

Botanical classification: *Ulmus davidiana* Japonica, cv. 'Discovery'.

Plant:

*Growth habit.*—Symmetrical, upright, vase-shaped which generally is exhibited from the initial lateral branch to the top of the crown. A major difference between the new 'Discovery' cultivar and other Japanese elm cultivars is the generally symmetrical growth habit and the generally upright disposition of the branches. A typical crotch angle is approximately 40 degrees. This can be compared to the open crown with codominant lateral branching of the 'Freedom' cultivar.

*Size.*—The tree at full maturity is believed to be capable of assuming a height and width of approximately 35 to 40 feet.

*Bark.*—Typical of the species.

Figure 4:
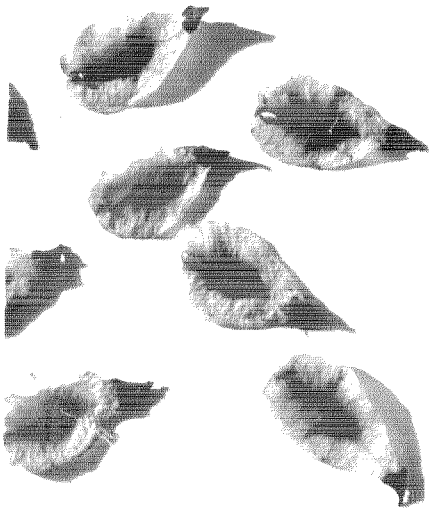
FIG. 4 illustrates typical seeds of the new cultivar of the present invention.

*Seed.*—See FIG. 4. Smaller than that of the American elm and typical of the species.

Foliage:

*Shape.*—Simple, obovate to oval with an acuminate apex and a base that is often nearly equilateral.

*Serration.*—Coarsely double serrate (as illustrated), but commonly less serrate than the 'Freedom' cultivar.

*Size.*—The leaves commonly are approximately 15 percent smaller than those of the 'Freedom' cultivar. Typical leaves of the 'Discovery' cultivar commonly average 7.4 cm. in length and approximately 5.3 cm. in width. This can be compared to an average typical length of approximately 8.9 cm. and an average typical width of approximately 6.4 cm. for the 'Freedom' cultivar.

Figure 1:
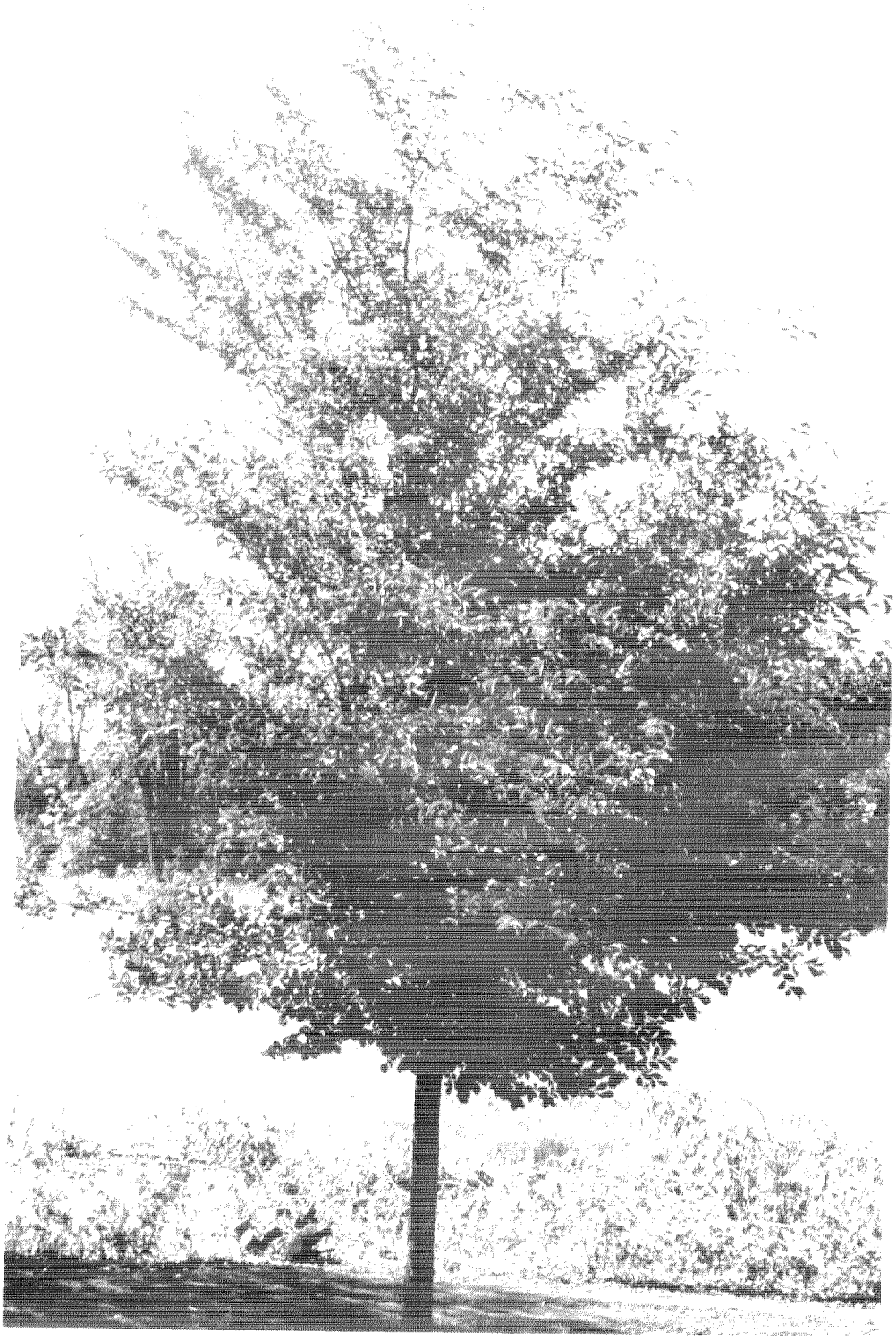
FIG. 1 illustrates the original tree of the new variety while growing at the Prairie Shade Nursery during the summer. The attractive symmetrical upright vase-shaped configuration of the tree is illustrated.
Figure 2:
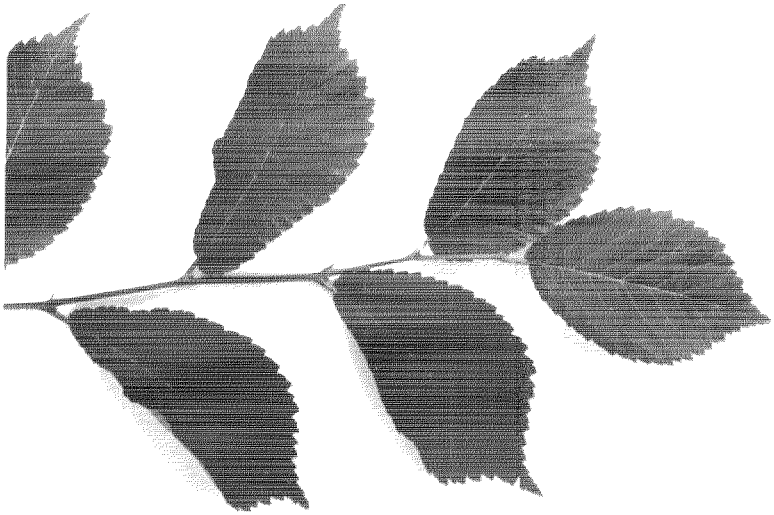
FIG. 2 illustrates a portion of a typical branch of the new cultivar during late June. The leaves are shown to have an obovate to oval configuration, coarse double serration, and an acuminate base that is nearly equilateral.
Figure 3:
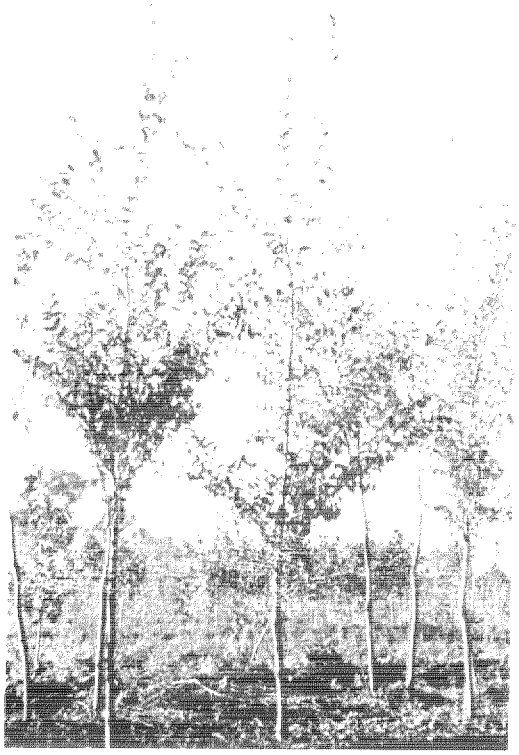
FIG. 3 illustrates during autumn young grafted trees of the new cultivar having a trunk diameter of approximately two inches wherein the more or less symmetrical configuration of the tree crowns are shown even at an early age. The trees in the foreground are approximately five years of age.

*Color.*—Medium green, yellow-green group 147A on the upper surface, and yellow-green group 147C on the under surface. During the autumn the leaves assume a yellow coloration. See FIG. 3 where some of the yellow autumn coloration is beginning to appear. The yellow autumn leaf coloration lacks the red-purple tinge that commonly is present on the leaves of the 'Freedom' cultivar during the fall.

Development:

*Vegetation.*—Slightly less vigor than the species which is believed to contribute to slightly more hardiness than that of previously available plants of the species. It has been found that a one year-old tree of the new 'Discovery' cultivar commonly produces a terminal growth of approximately 43.1 cm. This can be compared to an average terminal growth of approximately 48 cm. for the species.

*Disease resistance.*—High resistance to Dutch elm disease that is believed to be comparable to that of the 'Freedom' cultivar. Such disease resistance is maintained from the juvenile stage through maturity. More specifically, cultured stains of the most aggressive known forms of Dutch elm disease obtained from the University of Toronto were inoculated into trees of the new cultivar being grown at Portage la Prairie, Manitoba, Canada, on successive years during 1993 and 1994. As a result of such inoculation it was observed that a small amount of foliage tip die-back took place. Further study and analysis of the leaf tips has indicated that this condition of the tree likely was caused by natural toxins that were generated within the tree while combating the inoculations of fungus.

*Hardiness.*—Very good and is believed to slightly exceed that of the species. Is hardy in Zone 3 of the USDA Plant Hardiness Zone Map.

I claim:

1. A new and distinct variety of Japanese elm tree having the following combination of charateristics:

(a) exhibits an attractive symmetrical upright vase-shaped growth habit,
(b) forms foliage that is obovate to oval in configuration and is slightly smaller than is typical for the species,
(c) exhibits good cold hardiness, and
(d) is highly resistant to Dutch elm disease;

substantially as illustrated and described.

* * * * *